United States Patent [19]

Thenappan et al.

[11] Patent Number: 5,736,012
[45] Date of Patent: Apr. 7, 1998

[54] PROCESS FOR THE PREPARATION OF A FLUORINATED ACID

[75] Inventors: Alagappan Thenappan, Cheektowaga; Michael Van Der Puy, Amherst, both of N.Y.

[73] Assignee: AlliedSignal Inc., Morristown, N.J.

[21] Appl. No.: 711,774

[22] Filed: Sep. 10, 1996

[51] Int. Cl.$^6$ .......................... C07C 17/00; C07C 51/00; C07C 51/16; C07C 51/31
[52] U.S. Cl. .................. 204/157.94; 204/157.89; 562/542; 562/543; 562/544
[58] Field of Search .............. 204/157.6, 157.89, 204/157.95, 157.94; 562/542, 543, 544

[56] References Cited

FOREIGN PATENT DOCUMENTS

| 4-005247 | 1/1992 | Japan . |
| 98360 | 8/1978 | Poland . |

OTHER PUBLICATIONS

Allen, D.R., "Preparation of Trifluoroacetic Acid", *J. Org. Chem.*, 26, 1961, p. 923, Mar.

Banks, R.E. et al. "Organo Fluorine Chemistry–Principles and Commercial Applications" Plenum Press, New York, 1994, p. 133 *.

Haszeldine, R.N. and Nyman, R. "Oxidation of Polyhalogeno–compounds. Part II. Photolysis and Photochemical Oxidation of Some Chlorofluoroethanes," *J. Chem. Soc.* 1959, p. 387 *.

Haszeldine, R.N. and Nyman, R. "Oxidation of Polyhalogeno–compounds. Part III. Thermal Oxidation of Some Chlorofluoroethanes," *J. Chem. Soc.* 1959, p. 420 *.

Henne, A.L. and Renoll, M.W., "Fluoroethanes and Fluoroethylenes. V" *J. Am. Chem. Soc.*, 1936, p. 889, Jun.

Haszeldine et al., "Oxidation of Polyhalogeno–Compounds. PartII. Photolysis and Photochemical Oxidation of Some Chlorofluoroethanes", J. Chem. Soc., pp. 387–396, 7/1959.

*Primary Examiner*—Kathryn L. Gorgos
*Assistant Examiner*—Edna Wong
*Attorney, Agent, or Firm*—Jay P. Friedenson

[57] ABSTRACT

A process for the preparation of a fluorinated acid such as trifluoroacetic acid, including admixing an hydrofluorocarbon, such as 1,1,1-trifluoroethane, with chlorine, an oxidizing agent and an additive to prevent or minimize decomposition; and irradiating the reaction mixture with a light source having a wavelength ranging from 2000 Å to 14000 Å.

20 Claims, No Drawings

PROCESS FOR THE PREPARATION OF A FLUORINATED ACID

FIELD OF THE INVENTION

This invention relates to a process for the preparation of a fluorinated acid such as trifluoroacetic acid. In particular, the present invention provides a method for preparing trifluoroacetic acid via photochemical oxidation of 1,1,1-trifluoroethane with oxygen in the presence of chlorine and an additive to prevent or minimize decomposition of the initial oxidation products.

BACKGROUND OF THE INVENTION

Trifluoroacetic acid (i.e., $CF_3COOH$ or TFAA) is an important synthetic intermediate. It is used as a solvent for polymeric materials such as polypeptides, polyesters and cellulosic compounds, and as a catalyst for polymerization and condensation reactions. A trifluoroacetate group is used as a protective group in the amino-acid synthesis. Metal salts of trifluoroacetic acid find applications in the manufacturing of pharmaceuticals, insecticides and dyes. Sodium trifluoroacetate can be used as a gelling inhibitor at high temperatures in lubricants and hydraulic fluids.

There are a number of methods to prepare TFAA in the literature each having certain limitations. The preparation of TFAA in a 50% conversion by the direct oxidation of 1,1,1-trifluoroethane (i.e., $CF_3CH_3$ or HFC-143a) with air and water vapor using 15000 voltage electric discharge [Allen, D. R. *J. Org. Chem.*, 26, 1961, p. 923] is not practical for commercial scale-up. The production of TFAA from acetic acid and a little acetic anhydride using Carbon Anode Vapor phase Electrochemical fluorination (CAVE) technology requires the use of expensive, HF-resistant reactors and special handling techniques ["Organo Fluorine Chemistry— Principles and Commercial Applications" by Banks, R. E. et al., Plenum Press, New York, 1994]. The photochemical oxidation of 1-chloro-2,2,2-trifluoroethane (i.e., HCFC-133a) and 1,1-dichloro-2,2,2-trifluoroethane (i.e., HCFC-123) in the presence of chlorine gives a mixture of TFAA and trifluoroacetyl chloride [Haszeldine, R. N., Nyman, F. *J. Chem. Soc.*, 1959, p. 387]. The separation of trifluoroacetyl chloride from the by-product, viz., hydrogen chloride is very difficult. Although TFAA is the only product produced when the photooxidation of HCFC-123 and 133a is carried out in the presence of water and water and chlorine, the oxidations require long reaction times (72–174 hours). In the thermal oxidations of HCFCs 133a and 123 with oxygen and chlorine to produce TFAA [Haszeldine, R. N., Nyman, F. *J. Chem. Soc.*, 1959, p. 420], the acid decomposes at 250° C. to give a mixture of carbon dioxide and silicon tetrafluoride. Although hydrochlorofluorocarbons 133a and 123 have been oxidized to TFAA, oxidation of hydrofluorocarbon 143a to TFAA is not known in the art. In particular, the photochemical oxidation of HFC-143a to trifluoroacetic acid is not reported.

HFC-143a has an estimated lifetime of 50 years indicating a slow reaction with hydroxyl radicals. The bromination of HFC-143 a with elemental bromine to form 1-bromo-2,2,2-trifluoroethane requires very high temperatures (550°–800° C.) [Japanese Patent No. 4005247]. The chlorination of HFC-143a to form 1,1,1-trichloro-2,2,2-trifluoroethane requires UV light, heat (220°–230° C.) and the use of HCFC-123 as an initiator [Polish Patent 98360]. Therefore, based on the information in the literature, the discovery that the photochemical oxidation of HFC-143a in the presence of chlorine and an inventive additive at room temperature to yield TFAA with short reaction time is surprising.

The preparation of TFAA from 1,1,1-trifluoroethane via photochemical oxidation has several advantages over other methods. The starting material, HFC-143a can be readily prepared in a high yield from 1,1,1-trichloroethane (i.e., $CH_3CCl_3$ or methyl chloroform or HCC-140) [Henne, et al., *J. Am. Chem. Soc.*, 1936, p. 889] and the process is amenable to commercial scale-up. The photochemical oxidation of HFC-143a with oxygen in the presence of chlorine and an additive selected from the group including chlorocarbons, chlorofluorocarbons, perfluorocarbons, water and mixtures thereof produces TFAA in 2 hours. Unlike other methods, the process described herein does not require any special apparatus or a long reaction time. If necessary, anhydrous TFAA can be isolated in pure form by choosing appropriate additives.

SUMMARY OF THE INVENTION

The present invention provides a process for the preparation of fluorinated acids, such as trifluoroacetic acid by the photochemical oxidation of 1,1,1-trifluoroethane. The process comprises reacting 1,1,1-trifluoroethane with oxygen, chlorine and an additive to prevent or minimize decomposition of the initial oxidation products in the presence of light at wave lengths greater than about 2000 Å.

DETAILED DESCRIPTION OF THE INVENTION

The present invention provides a process to prepare fluorinated acids, such as trifluoroacetic acid via the photochemical oxidation of 1,1,1-trifluoroethane with oxygen in the presence of chlorine and an additive as described above. The process includes irradiating a mixture of HFC-143a with oxygen, chlorine and the additive, in a reactor using light at wave lengths greater than about 2000 Å.

The reactor to be used in the oxidation process according to the present invention should be constructed of a material which is resistant to attack by the reactants. Preferably, the reactor is constructed from glass. Since some of the starting materials used in this process are gases at ambient conditions, the reactor is made to withstand the vapor pressure of the reactants during the oxidation. A convenient laboratory apparatus for performing the photochemical oxidation is a pressure rated glass reactor with a water jacketed quartz immersion well into which the light source is placed. The glass reactor itself may also be jacketed for the control of the reaction temperature by using a circulating fluid for cooling. Suitable pressure rated glass reactors useful for the present invention are commercially available.

The source of irradiation for the photochemical oxidation is not critical and it may be provided by any conventional light sources such as mercury vapor lamps (high and medium pressure) and bright incandescent lamps. Although any type of irradiation such as X-rays and gamma rays may be used, ultraviolet light is preferred. The wave length of the light used should be greater than about 2000 Å and preferably from about 2200 to about 14000 Å.

The hydrofluorocarbon to be oxidized according to the present invention have the general formula: $[F(CF_2)n]CH_3$, wherein n=1–5. Examples of such hydrofluorocarbon include: $CF_3CH_3$; $CF_3CF_2CH_3$; $CF_3(CF_2)_2CH_3$; $CF_3(CF_2)_3CH_3$; and $CF_3(CF_2)_4CH_3$; with the preferred hydrofluorocarbon for the oxidation being 1,1,1-trifluoroethane.

The products resulting from the oxidation according to the present invention have the general formula: $[F(CF_2)_n]$ COOH, wherein n=1–5. Examples of such products include: $CF_3COOH$; $CF_3CF_2COOH$; $CF_3(CF_2)_2COOH$; $CF_3(CF_2)_3COOH$; and $CF_3(CF_2)_4COOH$; with the preferred product from the oxidation being trifluoroacetic acid.

The hydrofluorocarbons $CF_3CH_3$ and $CF_3CF_2CH_3$ are commercially available and can also be prepared by any of the processes generally known in the art. For example, $CF_3CH_3$ can be readily prepared in high yield from 1,1,1-trichloroethane (i.e., $CH_3CCl_3$ or methyl chloroform or HCC-140) by a literature procedure [Henne, et al., *J. Am. Chem. Soc.*, 1936, p. 889] and the process is amenable to commercial scale-up.

Chlorine gas used in the oxidation process acts as an initiator and it enables the irradiation time to be shortened. The chlorine gas used in the process is commercially available and the gas is used without any additional purification.

The additive used in the photochemical oxidation process can be any compound or composition which prevents or minimizes the decomposition of the initial oxidation products, such as acid halides, to form carbonyl halides, carbon dioxide and silicon tetrafluoride. The additive used should be inert under the reaction conditions and its physical properties should facilitate its separation from the product stream. The additives are preferably selected from the group including chlorocarbons, chlorofluorocarbons, perfluorocarbons, water and mixtures thereof; although any other compound or composition which accomplishes the aforementioned purpose can be used. Examples of suitable additives include: carbon tetrachloride, 1,1,2-trichloro-1,2,2-trifluoroethane, 1,2-dichloro-1,1,2,2-tetrafluoroethane, n-perfluoropentane, n-perfluorohexane, n-perfluoroheptane, n-perfluorooctane, water and mixtures thereof. In the process of the invention, preferred additives are: 1,1,2-trichloro-1,2,2-trifluoroethane, n-perfluoroheptane, water and a mixture of 1,1,2-trichloro-1,2,2-trifluoroethane and water with the most preferred additive being water and a mixture of 1,1,2-trichloro-1,2,2-trifluoroethane and water.

The oxidizing agent useful in the present invention is selected from air, molecular oxygen, and mixtures of nitrogen and oxygen. Preferably the oxidizing agent is either oxygen or air, with the most preferred oxidizing agent being oxygen. The oxidizing agents useful for the present invention are commercially available.

The hydrofluorocarbon to be oxidized in the present invention are either gases or liquids. The photochemical oxidation is effected by admixing the starting material with oxygen, chlorine and the additive in a glass reactor and irradiating the reaction mixture to a light source of suitable wave length for a specified period. The reactor pressure is monitored periodically and the decrease in pressure indicates the progress of the reaction. When there is no further decrease in pressure, the reaction is deemed complete.

Conversion of HFC-143a to trifluoroacetic acid depends on the length of irradiation of the reaction mixture. At the lower end of the irradiation time, the conversion is low and at the higher end, the amount of by-products increase and the selectivity is diminished. More preferably, the irradiation time ranges from about 2 hours to about 24 hours and most preferably from 2–12 hours.

The oxidation process for the present invention is conducted in the ambient temperature range. Although in principle, the temperature will affect the conversion of the starting materials to products, it is convenient to operate the oxidation process near the ambient temperature range. Preferably the temperature ranges from about 0° to about 100° C. and most preferably from about 20° to about 60° C.

Pressure is not critical for the present invention and the only pressure of the reactor is due to the vapor pressure of the reactants such as oxygen, chlorine and the starting material. As the reaction progresses, there is a decrease in pressure in the reactor indicating the consumption of the reactants.

Since the role of chlorine gas is to initiate the reaction of HFC-143a with oxygen, the molar ratio of chlorine to hydrofluorocarbon should be kept at minimum in order to limit the amount of unwanted by-products. Useful molar ratio of $Cl_2$/hydrofluorocarbon ranges from about 0.01 to about 1.0 and preferably the ratio is from about 0.01 to about 0.5.

Based on reaction stoichiometry, the required ratio of oxygen present in the oxidizing agent to hydrofluorocarbon is 1.5 and preferably the concentration of the oxygen be kept high to increase the conversion of the hydrofluorocarbon. Most preferred ratio of oxygen to hydrofluorocarbon ranges from about 2 to about 10.

Since the role of the additive is to prevent or minimize the decomposition of the initial oxidation products by converting them to more stable compounds or dissolving them, its quantity can vary within broad limits. Preferably, the weight ratio of the additive to hydrofluorocarbon ranges from about 5 to about 50 with the most preferred weight ratio being about 10 to about 25.

The weight percentage of water in the mixture of 1,1,2-trichloro-1,2,2-trifluoroethane and water ranges from about 2 to about 80 weight % based on the quantity of additive used for the oxidation with the most preferred range being about 20 to about 50 weight %.

The oxidation process for the present invention is preferably operated in such a way that either the chlorine conversion is high or unreacted chlorine is returned to the reactor. Similarly the process is operated in such a way that unused oxidizing agent is returned to the reactor. The oxidation process according to the present invention may be carried out either as a batch or a continuous process.

The resulting oxidized acid and the additive may be separated from the reaction mixture via any known separation or purification method known in the art such as distillation.

EXAMPLES

The following examples serve to illustrate the invention, but are not intended to limit the scope of the invention.

Example 1

A 90 ml. pressure rated glass reactor equipped with a magnetic stir bar and a pressure gauge was charged with 10.3 g water, cooled to −78° C., evacuated under vacuum and then sequentially charged with 0.9 g HFC-143a (10.7 mmoles), 0.3 g Cl2 (4.2 mmoles) and 1.4 g O2 (43.8 mmoles). The resultant mixture was stirred, allowed to warm to room temperature and then irradiated with a 450 Watt, high pressure Hanovia lamp for 6 hours. Upon illumination, a decrease in pressure (ΔP=30 psi) with concomitant formation of a green liquid in the reactor was observed. When there was no further drop in pressure, the reactor was cooled to −78° C. and after venting the non-condensable vapors, 11.9 g green solution was obtained which was analyzed by GC, and $^{19}F$ NMR. GC: 143a (1.1%), $CF_3COOH$ (97%) and siloxanes (2.0%). $^{19}F$ NMR [$(CD)_3CO$, $CFCl_3$ int.]: −70.9 ppm (s, $CF_3COOH$).

Example 2

As described in example 1, the reactor was charged with 0.8 g HFC-143a (9.5 mmoles), 0.3 g $Cl_2$ (4.2 mmoles) and 2.2 g O2 (68.8 mmoles) and irradiated with the same mercury vapor lamp for 20 hours at room temperature. Upon illumination, a decrease in pressure (ΔP=7 psi) in the reactor with concomitant formation of a few drops of green liquid in the reactor was observed. GC-MS of the reaction mixture dissolved in acetonitrile, after normalizing for the solvent indicated the following: 143a (88.7%), CF$_3$COOH (9.4%), CCl$_4$ (0.6%), CF$_2$ClCFCl$_2$ (0.7%) and unknown (0.6%). The conversion of HFC-143a to CF$_3$COOH is low in the absence of water as indicated in this example.

Example 3

As described in example 1, the reactor was initially charged with 10.1 g n-perfluoroheptane, cooled and then charged with 1.4 g HFC-143a (16.7 mmoles), 0.6 g Cl$_2$ (8.5 mmoles) and 1.2 g O$_2$ (37.5 mmoles). Irradiation of the reaction mixture with the mercury vapor lamp for 7 hours at room temperature decreases the pressure by 15 psi (ΔP=15 psi). GC-MS of the reaction mixture after normalizing for the solvent indicated the following: 143a (68.5%), CF$_3$COOH (26.6%), HCFC-133a (1.9%), and CF$_2$ClCFCl$_2$ (1.6%). This example illustrates the use of n-perfluoroheptane as a solvent for photochemical oxidation.

Example 4

As described in example 3, the reactor was initially charged with 10.5 g 1,1,2-trichloro-1,2,2-trifluoroethane (CFC-113) and 1.0 g water. The reactor was then cooled to −78° C., evacuated and charged with 3.0 g HFC-143a (35.7 mmoles), 0.6 g Cl2 (8.5 mmoles) and 1.2 g O$_2$ (37.5 mmoles). Irradiation of the reaction mixture with the mercury vapor lamp for 6 hours at room temperature decreases the pressure by 20 psi (ΔP=20 psi). $^{19}$F NMR analysis [(CD$_3$)$_2$CO, CFCl$_3$] of the organic layer indicated the following: −63.8 ppm (d), −67.8 ppm (t) and −72.2 ppm (s). GC of the aqueous layer after normalizing for the solvent indicated the following: 143a (48%), CF$_3$COOH (43.7%), 133a (3.8%). CF$_3$COOH was present in both organic and aqueous layers. This example illustrates the use of a mixture of CFC-113 and water as a solvent system for the oxidation.

Example 5

As described in example 1, the reactor was initially charged with 10.8 g water and then cooled to −78° C. After evacuating the reactor it was charged with 1.6 g HFC-143a (19.0 mmoles), 0.8 g Cl$_2$ (11.3 mmoles) and 1.0 g O$_2$ (31.3 mmoles). Irradiation of the reaction mixture with the mercury vapor lamp for 2 hours at room temperature decreases the pressure by 60 psi (ΔP=60 psi). GC of the reaction mixture indicated the following: 143a (32.6%), CF$_3$COOH (60.8%), high boiling unknown (6.6%). $^{19}$F NMR analysis of the reaction mixture dissolved in deuterated acetone [(CD$_3$)$_2$CO, CFCl$_3$]: −70.8 ppm (s, CF$_3$COOH), −79.7 ppm (s). This example illustrates the effect of irradiation time (2 h) on the conversion of HFC-143 a to trifluoroacetic acid.

What is claimed is:

1. A process for the preparation of a fluorinated acid comprising the steps of:

(a) admixing a hydrofluorocarbon of the formula F(CF$_2$)$_n$CH$_3$, wherein n=1–5, with an oxidizing agent, chlorine and an additive to form a reaction mixture; and (b) irradiating the said reaction mixture with a light source having a wavelength from about 2000 Å to about 14000 Å to produce said fluorinated acid.

2. A process for the preparation of a fluorinated acid in accordance with claim 1, wherein said hydrofluorocarbon is 1,1,1-trifluoroethane.

3. A process for the preparation of a fluorinated acid in accordance with claim 1, wherein said fluorinated acid has a general formula:

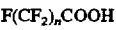

F(CF$_2$)$_n$COOH wherein n=1–5.

4. A process for the preparation of a fluorinated acid in accordance with claim 1, wherein said fluorinated acid is trifluoroacetic acid.

5. A process for the preparation of a fluorinated acid in accordance with claim 1, wherein said oxidizing agent is selected from the group consisting of air, molecular oxygen and mixtures of nitrogen and oxygen.

6. A process for the preparation of a fluorinated acid in accordance with claim 1, wherein said oxidizing agent is oxygen.

7. A process for the preparation of a fluorinated acid in accordance with claim 1, wherein said additive is selected from the group consisting of chlorocarbons, chlorofluorocarbons, perfluorocarbons, water and mixtures thereof.

8. A process for the preparation of a fluorinated acid in accordance with claim 1, wherein said additive is selected from the group consisting of 1,1,2-trichloro-1,2,2-trifluoroethane, n-perfluoroheptane, water and a mixture of 1,1,2-trichloro-1,2,2-trifluoroethane and water.

9. A process for the preparation of a fluorinated acid in accordance with claim 1, wherein said additive is a mixture of 1,1,2-trichloro-1,2,2-trifluoroethane and water.

10. A process for the preparation of a fluorinated acid in accordance with claim 1, wherein the said wavelength of said light used for irradiation is from about 2200 Å to about 14000 Å.

11. A process for the preparation of a fluorinated acid in accordance with claim 1, wherein said process is carried out at temperatures ranging from about 0° C. to about 100° C.

12. A process for the preparation of a fluorinated acid in accordance with claim 1, wherein said reaction mixture is irradiated for a period of from about 2 to about 24 hours.

13. A process for the preparation of a fluorinated acid in accordance with claim 1, wherein molar ratio of chlorine to hydrofluorocarbon is from about 0.01 to about 1.0.

14. A process for the preparation of a fluorinated acid in accordance with claim 1, wherein molar ratio of said oxidizing agent to hydrofluorocarbon is from about 2 to about 10.

15. A process for the preparation of a fluorinated acid in accordance with claim 1, wherein a weight ratio of said additive to hydrofluorocarbon is from about 5 to about 50.

16. A process for the preparation of a fluorinated acid in accordance with claim 1, wherein the additive is an additive mixture comprising water, and a weight percentage of water in the additive mixture is from about 2 to about 80 weight % based on the quantity of the additive mixture.

17. A process for the preparation of a fluorinated acid in accordance with claim 1, wherein said hydrofluorocarbon is admixed with said oxidizing agent and said chlorine over an additive mixture of 1,1,2-trichloro-1,2,2-trifluoroethane and water in a pressure rated glass reactor at ambient temperature to form a reaction mixture and irradiating the said reaction mixture with a high pressure mercury vapor lamp for about 2–12 hours to produce trifluoroacetic acid.

18. A process for the preparation of a fluorinated acid in accordance with claim 17, wherein a molar ratio of said chlorine to said hydrofluorocarbon is from about 0.01 to about 0.5, a molar ratio of said oxidizing agent to said hydrofluorocarbon is from about 2.0 to about 10.0, a weight ratio of said additive to said hydrofluorocarbon is from about 10 to 25 and a weight percentage of water in the said additive mixture is from about 20 to about 50.

19. A process for the preparation of a fluorinated acid in accordance with claim 17, wherein said hydrofluorocarbon is 1,1,1-trifluoroethane, wherein a molar ratio of said chlorine to 1,1,1-trifluoroethane is from about 0.01 to about 0.5, a molar ratio of said oxidizing agent to 1,1,1-trifluoroethane is from about 2.0 to about 10.0, the weight ratio of said additive to 1,1,1-trifluoroethane is from about 10 to 25 and a weight percentage of water in the said additive mixture is from about 20 to about 50.

20. A process for the preparation of a fluorinated acid in accordance with claim 1, wherein a molar ratio of said chlorine to said hydrofluorocarbon is from about 0.01 to about 0.5, a molar ratio of said oxidizing agent to said hydrofluorocarbon is from about 2.0 to about 10.0, a weight ratio of said additive to said hydrofluorocarbon is from about 10 to 25.

* * * * *